April 25, 1972 F. W. ANDERSON Plant Pat. 3,130
ALMOMD TREE
Filed May 14, 1970
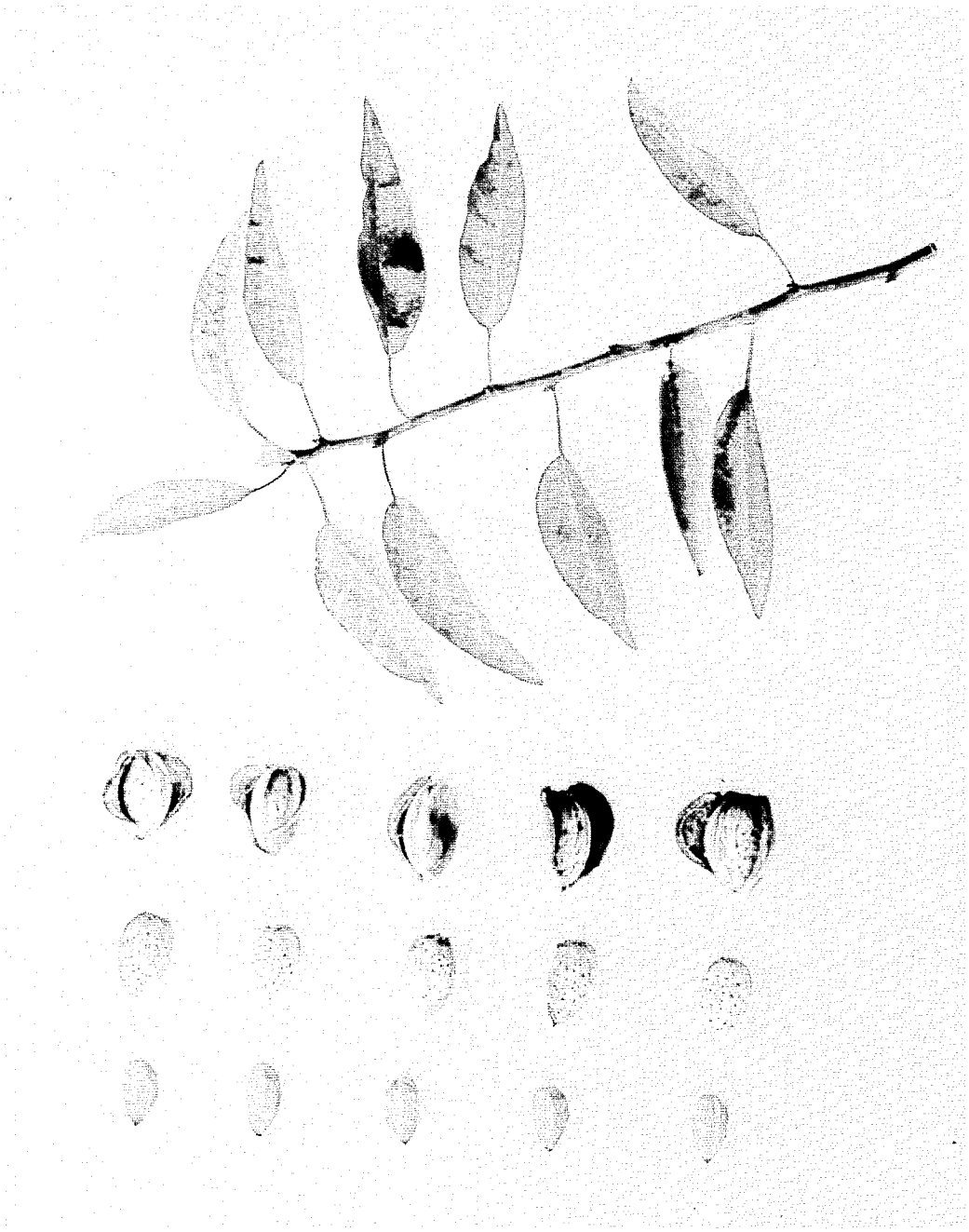
INVENTOR
Frederic W. Anderson
BY
Webster & Webster
ATTORNEYS United States Patent Office Plant Pat. 3,130
Patented Apr. 25, 1972

3,130

ALMOND TREE

Frederic W. Anderson, Merced, Calif., assignor to Arthur Bright, Le Grand, Calif.

Filed May 14, 1970, Ser. No. 37,357
Int. Cl. A01h 5/00
U.S. Cl. Plt.—30 1 Claim

ABSTRACT OF THE DISCLOSURE

A dense, medium size, vigorous almond tree having a medium to upright branching habit, abundant foliage with small ovate leaves, heavy white bloom, and small, well-sealed nuts borne regularly and heavily in clusters on short spurs, and in harvest before the Mission (unpatented); the variety being self-fertile, and having substantial resistance to spring frost damage.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of nut trees. The present variety of almond tree resulted from my endeavors in the conduct of such plant breeding program.

ORIGIN OF THE VARIETY

The herein claimed variety of almond tree was originated by me, in my experimental nursery and orchard located as aforesaid, in the following manner:

Since all present varieties of almond trees are self-sterile, I first crossed almonds with peaches; the latter being self-fertile. While the $F_1$ generation of such crosses were apparently all self-fertile and with viable seeds, the $F_2$ generation was nearly all self-sterile and extremely variable. However, by backcrossing the self-fertile trees of both of such generations with standard almond varieties, a considerable number of seedlings were obtained which were self-fertile. The instant variety is a selection of one of such seedlings and is now bearing heavily in my said experimental orchard.

ASEXUAL REPRODUCTION OF THE VARIETY

Subsequent to origination and selection by me of the present variety of almond tree, in the manner above described, I asexually reproduced it by grafting on mature trees in my said experimental orchard, and in maturity such reproductions ran true to the original tree in all respects.

SUMMARY OF THE VARIETY

The herein claimed variety of almond tree is dense, medium size, vigorous, medium to upright in branching habit, abundant of foliage with small ovate leaves, white and heavy of bloom, and a regular and heavy producer of small, well-sealed nuts borne in clusters on short spurs, and in harvest before the Mission; the variety being self-fertile, and evidencing substantial resistance to spring frost damage as compared to present standard varieties of almond trees. The present variety of almond tree produced good crops in years when spring frosts destroyed the crop on adjoining trees of such standard varieties.

It is believed that the present variety is the first self-fertile almond tree capable of successful commercial adaptation; the self-fertility of the variety assuring of more economical production of almond crops.

BRIEF DESCRIPTION OF THE DRAWING

The drawing is an illustration, by photographic reproduction in color, of a twig with leaves, nuts in hull, nuts out of hull, and separate kernels.

DESCRIPTION OF THE VARIETY

The botanical details of this new and distinct variety of almond tree—with color definitions (except those in common color terms) referenced to Maerz and Paul Dictionary of Color—are as follows:

Tree:
- *Density.*—Dense.
- *Size.*—Medium.
- *Vigor.*—Vigorous.

Trunk:
- *Form.*—Stocky.
- *Texture.*—Medium.

Branches:
- *Form.*—Stocky.
- *Texture.*—Medium.
- *Branching habit.*—Medium to upright.
- *Color.*—New wood—red. Mature wood—brown.

Foliage: Quantity—Abundant.

Leaves:
- *Size.*—Small; average length—2¾"; average width—¾".
- *Shape.*—Ovate.
- *Thickness.*—Medium.
- *Texture.*—Smooth.
- *Margin.*—Crenate.
- *Petiole.*—Medium length; medium thickness.
- *Glands.*—Number—1 to 4; alternate; small; positioned on petiole and base of blade.
- *Color.*—Top side—Medium green (22–J–6). Under side—Lighter green (22–K–5).

Bloom:
- *Amount of Bloom.*—Heavy.
- *Color.*—White.
- *Blooming Period.*—February 25–March 12, 1970. Usually 2 or 3 days before Mission, and 2 or 3 days after Nonpareil (unpatented).

Crop:
- *Bearing.*—Regular bearer.
- *Productivity.*—Heavy.
- *Distribution of nuts on tree.*—In clusters on short spurs.
- *Harvest period.*—Before Mission.
- *Tenacity.*—Hangs well on tree; easy to harvest; easy to shell.

Hull:
- *Other surface.*—Smooth.
- *Form.*—Regular.
- *Thickness.*—Thin.
- *Flesh.*—Tough.
- *Suture.*—Ridged.
- *Dehiscence.*—Opens freely.
- *Splitting.*—Along suture.

Nut:
- *Size.*—Small; average length—1⅛"; average width—⅝"; average thickness—½"; average weight—approximately 16 to an ounce.
- *Form.*—Length/width—ovate. Width/thickness—medium.
- *Shell.*—Soft to hard; thin. Outer shell—hard. Inner shell—well sealed.
- *Color.*—Medium light tan (12–I–7).
- *Pits.*—Small; numerous; shallow; irregular.
- *Base.*—Square to ventrally oblique.
- *Stem scar.*—Small.
- *Apex.*—Obtuse.
- *Wing.*—Broad; thin.
- *Inner surface.*—Medium color.
- *Percentage of kernel to nut.*—Averages approximately 52%.

Kernel:

*Size.*—Medium to small; average length—⅞"; average width—⅝"; average thickness—⅜"; average weight—approximately 32 to an ounce.

*Form.*—Length/width—Oval to ovate. Width/thickness—Medium.

*Base.*—Ventrally oblique.

*Stem scar.*—Small.

*Apex.*—Obtuse.

*Texture.*—Smooth to wrinkled.

*Pellicle.*—Thin.

*Pubescence.*—Medium.

*Color.*—Medium light brown (13–G–8).

*Number of doubles.*—Medium.

*Flavor.*—Normal.

*Quality.*—Medium.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, which is dense, medium in size, vigorous, medium to upright in branching habit, abundant of foliage with small ovate leaves, white and heavy of bloom, and a regular and heavy producer of small, well-sealed nuts borne in clusters on short spurs, and in harvest before the Mission; the variety being self-fertile, and having substantial resistance to spring frost damage as compared to present standard varieties.

No references cited.

ROBERT E. BAGWILL, Primary Examiner